United States Patent [19]
Goldfarb

[11] Patent Number: 5,955,016
[45] Date of Patent: Sep. 21, 1999

[54] METHOD OF FORMING A VASCULAR PROSTHETIC STRUCTURE INCLUDING EXPANDED PTFE AND GRAPHITE

[76] Inventor: David Goldfarb, 5926 N. 33rd St., Paradise Valley, Ariz. 85253

[21] Appl. No.: 08/468,435

[22] Filed: Jun. 6, 1995

Related U.S. Application Data

[63] Continuation of application No. 08/230,602, Apr. 21, 1994, abandoned, which is a continuation of application No. 07/920,124, Jul. 24, 1992, which is a continuation of application No. 07/799,385, Nov. 27, 1991, abandoned, which is a continuation of application No. 07/648,204, Jan. 31, 1991, abandoned, which is a continuation of application No. 07/537,341, Jun. 13, 1990, abandoned, which is a continuation of application No. 07/432,038, Nov. 3, 1989, abandoned, which is a continuation of application No. 07/328,569, Mar. 27, 1989, abandoned, which is a continuation of application No. 07/174,588, Mar. 29, 1988, abandoned, which is a continuation of application No. 07/081,659, Aug. 4, 1987, abandoned, which is a continuation of application No. 06/908,995, Sep. 18, 1986, abandoned, which is a continuation of application No. 06/807,834, Dec. 11, 1985, abandoned, which is a continuation of application No. 06/726,140, Apr. 23, 1985, abandoned, which is a continuation of application No. 06/633,143, Jul. 23, 1984, abandoned, which is a continuation of application No. 06/467,872, Feb. 18, 1983, abandoned, which is a continuation of application No. 06/292,906, Aug. 14, 1981, abandoned, which is a continuation of application No. 06/136,693, Apr. 2, 1980, abandoned, which is a continuation of application No. 05/862,816, Dec. 21, 1977, abandoned, which is a continuation-in-part of application No. 05/517,415, Oct. 24, 1974.

[51] Int. Cl.⁶ .............................. B29C 47/00; C08J 9/00; G09B 2/06; G09B 2/24
[52] U.S. Cl. ........................................ 264/127; 264/288.8
[58] Field of Search .................................. 264/127, 288.8

[56] References Cited

U.S. PATENT DOCUMENTS

| | | | |
|---|---|---|---|
| 2,782,180 | 2/1957 | Weidman | 264/127 |
| 3,054,761 | 9/1962 | Moore et al. | 264/127 |
| 3,473,087 | 10/1969 | Slade . | |
| 3,585,647 | 6/1971 | Gajewski et al. . | |
| 3,658,976 | 4/1972 | Slade | 264/127 |
| 3,846,353 | 11/1974 | Grotta | 424/183 |
| 3,953,566 | 4/1976 | Gore | 264/505 |
| 3,962,153 | 6/1976 | Gore | 264/127 |
| 3,971,134 | 7/1976 | Bokros | 32/10 A |
| 3,992,725 | 11/1976 | Homsy . | |
| 4,118,532 | 10/1978 | Homsy . | |
| 4,129,470 | 12/1978 | Homsy . | |
| 4,156,127 | 5/1979 | Sako et al. . | |
| 4,209,480 | 6/1980 | Homsy | 264/127 |
| 4,478,665 | 10/1984 | Hubis | 156/229 |

FOREIGN PATENT DOCUMENTS

| | | | |
|---|---|---|---|
| 686438 | 1/1953 | United Kingdom | 264/127 |

OTHER PUBLICATIONS

Thompson et al., "Paste Extrusion", Modern Plastics, Feb. 1956.

Soyer et al., A New Venous Prosthesis, Surgery, 72:864, 1972.

(List continued on next page.)

*Primary Examiner*—Catherine Timm
*Attorney, Agent, or Firm*—Wolf, Greenfield & Sacks, P.C.

[57] ABSTRACT

A method of forming a vascular prosthetic structure, including steps of: mixing polytetrafluoroethylene resin with graphite powder to create a mixture; compacting the mixture to form a preform; extruding the preform to form an extrudate, expanding the extrudate to form an expanded structure having a plurality of irregularly spaced nodes interconnected by fibrils; and sintering the expanded structure to form the vascular prosthetic structure.

10 Claims, 2 Drawing Sheets

OTHER PUBLICATIONS

"Heparin application to graphite–coated intravascular prostheses", Whiffen, M.D., James D., et al., Surgery, Aug. 1964, pp. 404–412.

"Present Status of Carbon Grafts", Sharp, William V., Chapter 26, pp. 326–330.

"Pyrolytic Carbon–Coated Grafts", Sharp, M.D., William V. and Teague, Phillip C., From the Northeastern Ohio Universities College of Medicine, Rootstown, and Vascular Research Laboratory, Akron City Hospital, Akron, Ohio.

"ULTI Carbon Goretex: A New Vascular Graft", Deusei, M.D., Robert, et al., From the University of Pittsburgh School of Medicine and Carbomedics, Inc., Pittsburgh, Pennsylvania, Current Surgery, May–Jun. 1983, pp. 198–199.

"Update on Carbon–Coated Grafts", Sharp, William V., Modern Vascular Grafts, Chapter 11, pp. 215–224.

METHOD OF FORMING A VASCULAR PROSTHETIC STRUCTURE INCLUDING EXPANDED PTFE AND GRAPHITE

This application is a continuation of application Ser. No. 08/230,602, filed Apr. 21, 1994, entitled GRAPHITE IMPREGNATED PROSTHETIC VASCULAR GRAFT MATERIALS, now abandoned, which is a continuation of application Ser. No. 07/920,124, filed Jul. 24, 1992, which is a continuation of application Ser. No. 07/799,385 filed Nov. 27, 1991 now abandoned, which is a continuation of application Ser. No. 07/648,204 filed Jan. 31, 1991, now abandoned, which is a continuation of application Ser. No. 07/537,341 filed Jun. 13, 1990, now abandoned, which is a continuation of application Ser. No. 07/432,038 filed Nov. 3, 1989, now abandoned, which is a continuation of application Ser. No. 07/328,569 filed Mar. 27, 1989, now abandoned, which is a continuation of application Ser. No. 07/174,588 filed Mar. 29, 1988, now abandoned, which is a continuation of application Ser. No. 07/081,659 filed Aug. 4, 1987, now abandoned, which is a continuation of application Ser. No. 06/908,995 filed Sep. 18, 1986, now abandoned, which is a continuation of application Ser. No. 06/807,834 filed Dec. 11, 1985, now abandoned which is a continuation of application Ser. No. 06/726,140 filed Apr. 23, 1985, now abandoned, which is a continuation of application Ser. No. 06/633,143 filed Jul. 23, 1984, now abandoned, which is a continuation of application Ser. No. 06/467,872 filed Feb. 18, 1983, now abandoned, which is a continuation of application Ser. No. 06/292,906 filed Aug. 14, 1981, now abandoned, which is a continuation of application Ser. No. 06/136,693 filed Apr. 2, 1980, now abandoned, which is a continuation of application Ser. No. 05/862,826 filed on Dec. 21, 1977, now abandoned, which is a continuation-in-part of application Ser. No. 05/517,415 filed on Oct. 24, 1974.

BACKGROUND OF THE INVENTION

This invention relates to materials for use in prosthetic vascular grafts, vascular structures made from such materials, and to the art of using such materials and structures.

The art of preparing prosthetic devices made of various plastics for use as vascular grafts is well developed. Prior art workers have widely investigated plastic substances for such use. One of the common problems encountered by them in the implantation of a vascular prosthesis is the failure of the graft by reason of thrombosis at the site of the graft. Among the causes of arterial graft failures due to arterial thrombosis are biological imcompatibility and insufficient flow or velocity through the graft caused by an inadequate inflow and/or outflow and turbulence at the site of the graft. To overcome such baleful influences it would be desirable to lend thromboresistant properties to the bloodstream-graft interface.

Much work has been done on the problem by prior art workers. In 1961 Gott and his co-workers determined that graphite placed in the bloodstream reduced thrombosis. See Gott, B. L., et al, "The Coating of Intravascular Plastic Prosthesis with Colloidal Graphite", Surgery 50: 382, 1961. The authors attributed such thromboresistance to the electronegative conductivity of the graphite. They further suggested that the conductivity of graphite dissipates a positive charge and that the bloodstream-graphite interface possesses a negative charge. This concept was subsequently confirmed by others.

The significance is that cellular blood elements, as well as fibrinogen and platelets, are known to be negatively charged at the normal pH in the blood. Natural intima (the natural bloodstream lining) is negative in charge with respect to the adventitia, and it is generally thought that this relative negativity plays a significant role in natural anti-thrombogenesis. These concepts are treated in greater detail in the following treatises.

Leininger, R. I. Surface effects in blood-plastic compatibility. Chapter in Biophysical Mechanisms in Vascular Homeostasis and Intravascular Thrombosis (Ed. P. N. Sawyer), Appleton-Century-Crofts, New York, 1965, pp 288–294.

Milligan, H. L., Davis, J. W., and Edmark, K. W. The search for the nonthrombogenic property of colloidal graphite. J. Biomed. Mater. Res., 4: 121, 170.

Gott, V. L., Whiffen, J. D., Dutton, R. C., Leininger, R. I., and Young, W. P. Biophysical studies on various graphite-benzalkonium-heparin surfaces. Chapter in Biophysical Mechanisms in Vascular Homeostasis and Intravascular Thrombosis (Ed. P. N. Sawyer), Appleton-Century-Crofts, New York, 1965, pp 297–305.

Sawyer, P. N., Brattain, W. H., and Boddy, P. J. Electrochemical criteria in the choice of materials used in vascular prostheses. Chapter in Biophysical Mechanisms in Vascular Homeostasis and Intravascular Thrombosis (Ed. P. N. Sawyer), Appleton-Century-Crofts, New York, 1965, pp 337–348.

Sawyer, P. N. and Pate, J. W. Bioelectric phenomena in intravascular thrombosis. Am. J. Physiol., 175: 103, 1953.

As appears from the references, as early as 1953 Sawyer and Pate reported that clotting is caused by a reversal of the normally negative charge on the intima with respect to the adventitia. In 1965 Leininger verbalized the idea that to prevent the deposition of blood elements on vessel walls the prosthetic should have a negative charge.

Over the years attempts were made to provide prosthetic vascular grafts with a negative charge, with varying degrees of success or lack of it. Pure graphite devices have been used, but they have the disadvantages of being rigid and so their use is extremely limited, e.g., mechanical components of heart valves. Coated flexible tubes have been tried experimentally with only temporary success. The general problem is that in use the bloodstream leaches graphite from the graphite-treated vascular prosthetic and thrombosis thereafter develops. Fracture from manipulation of the rigid graphite lining on the flexible substrate form emboli in the bloodstream, presenting further complications.

Although there existed a need and desire for a vascular prosthetic device having graphite permanently bound to the prosthetic, particularly in flexible vascular grafts, no one in the prior art succeeded in devising a satisfactory solution.

It is, therefore, seen that a longstanding, but un-met, need for a negatively charged plastic prosthetic that will not leach out the graphite existed at the time of the making of this invention, notwithstanding the attention given to the problem by a number of gifted researchers.

BRIEF DESCRIPTION OF THE INVENTION

The instant invention, which meets the longstanding, felt needs of the art, resides in the provision of a composition of matter for use in making a prosthetic vascular device, the composition being a suitable biologically compatible plastic material having a negative charge, suitably by means of the plastic's combination with a biologically compatible negatively charged material, such as graphite, that is incorporated into the plastic material, preferably in the framework of the lattice of the plastic material. In a further aspect of the invention there are provided prosthetic vascular devices made from said compositions. A preferred embodiment of the composition is a combination of plastic (a preferred plastic is expanded polytetrafluoroethylene hereinafter referred to as PTFE) and graphite (colloidal carbon) in a ratio of 9:1.

The composition is made by mixing the plastic resin with the graphite in dry form, resulting in a homogeneous mixture, and thereafter processing the combination by steps known to the art for processing the plastic alone, e.g., PTFE.

In preparing a PTFE composition according to the teachings of the instant invention, PTFE-resin powder and negatively charged substance, e.g., graphite powder, are thoroughly shaken to achieve a homogeneous mixture, preferably at a 9:1 ratio. After mixing, the resin-graphite combination is processed in the standard manner of processing PTFE powder into preforms.

A method of processing finely powdered tetrafluoroethylene resin to produce thin-wall tubing by ram extrusion, adaptable to making the compositions of this invention, is set out in "Paste Extrusion", by Thompson and Stabler, Feb., 1956, *Modern Plastics*. This method may be used to process the PTFE and graphite powders into preform shapes. See also *Modern Fluoroplastics; Plastics Encyclopedia*, 1977–1978, p. 26; "Extrusion Properties of Lubricated Resin from Coagulated Dispersion", Lantz, et al, *Industrial and Engineering Chemistry; Encyclopedia of Chemical Technology*, Vol. 9, 2d Ed., p. 805.

Briefly, in adapting the prior art method to this invention, an extrusion grade PTFE fine powder and a graphite powder are blended with an extrusion aid such as VM and P grade naptha and the composition is preformed to a cylindrical billet under 100 to 300 p.s.i. The preform composition is then placed in a ram-type extruder and forced through a forming die by the ram; then the extrusion aid is vaporized at 200 to 575° F.

Thereafter, the fragile extrudate may be sintered and cooled to form the finished shape, e.g., rigid heart valves, or further processed to provide an expanded PTFE tube according to the teachings of my co-pending U.S. application Ser. No. 517,415, filed Oct. 24, 1974, for use as flexible, permanent, venous, arterial and heart grafts.

For example, a particularly useful application and embodiment of this invention is in its adaptation for use in a device such as described in my said pending application which teaches a prosthetic vascular device formed from a small bore tube of PTFE without graphite which has been heated, expanded and sintered so as to have a microscopic superstructure of uniformly distributed nodes interconnected by fibrils and characterized by: a) an average internodal distance with is (i) large enough to allow transmural migration of typical red cells and fibroblast, and (ii) small enough to inhibit both transmural blood flow at normal pressures and excessive clot formation; b) an average wall thickness which (i) small enough to provide proper mechanical conformity to adjacent cardiovascular structures, and (ii) large enough, when taken in conjunction with the associated internodular distance, to prevent leakage and clot formation, to allow free and uniform transmural nutrient flow, and to assure mechanical strength and ease of implantation.

In a particularly preferred embodiment there is provided a prosthetic vascular structure made of highly expanded PTFE having graphite incorporated into the framework of its lattice. The structure has a macroscopically tubular configuration with proximal and distal ends, and a microscopic superstructure of irregularly spaced nodes of various sizes and shapes interconnected by fibrils; the vascular structure is further characterized by an average wall thickness in the range between about 0.2 and 1.5 mm. a substantially uniform distribution or nodes throughout the tubular configuration, an average density between the range 0.2 and 0.7 grams per millimeter, and an average distance between notes small enough to prevent transmural blood flow and thrombosis but no less than the approximate dimension of a red blood cell. Thus, means are provided for smoothly conveying the flow of blood between at least two points in a living organism while sharing and controlling cellular ingrowth through the wall of the tubular configuration to promote and nourish a thin, viable neointima over the inner surface thereof and to firmly attach the prosthetic vascular structure to adjacent tissue of the living organism.

The nodes in the vascular structure may be generally ellipsoidal in shape with an average dimension along their minor axes less than three times the maximum dimension of an average red cell. This average will be less than eighteen microns, typically. The major axes of the nodes in the vascular structure are in a generally radial orientation with respect to the tubular configuration which has an average inside diameter of about 40 mm. as a practical maximum. The inside diameter will usually be less than eight millimeters and more commonly between two and six millimeters. The structure's tensile strength is in the range between 2500 and 6500 p.s.i. It also may taper from a first inside diameter at the proximal end to a second inside diameter at the distal end. The inside diameter ranges between 5 and 8 mm. at the first inside diameter and between 2 and 6 mm. at the second inside diameter. Further explanation of the functions of the various parameters set out above may be found in my referenced co-pending application, Ser. No. 517,415, filed Oct. 24, 1974, particularly pages 9 through 18.

BRIEF DESCRIPTION OF THE DRAWING

The various objects and advantages of the invention, and the method of making and using the invention, will be more fully understood from a consideration of the following detailed description in view of the attached illustrations wherein.

DETAILED DESCRIPTION OF THE PREFERRED EMBODIMENTS

Figure 1:
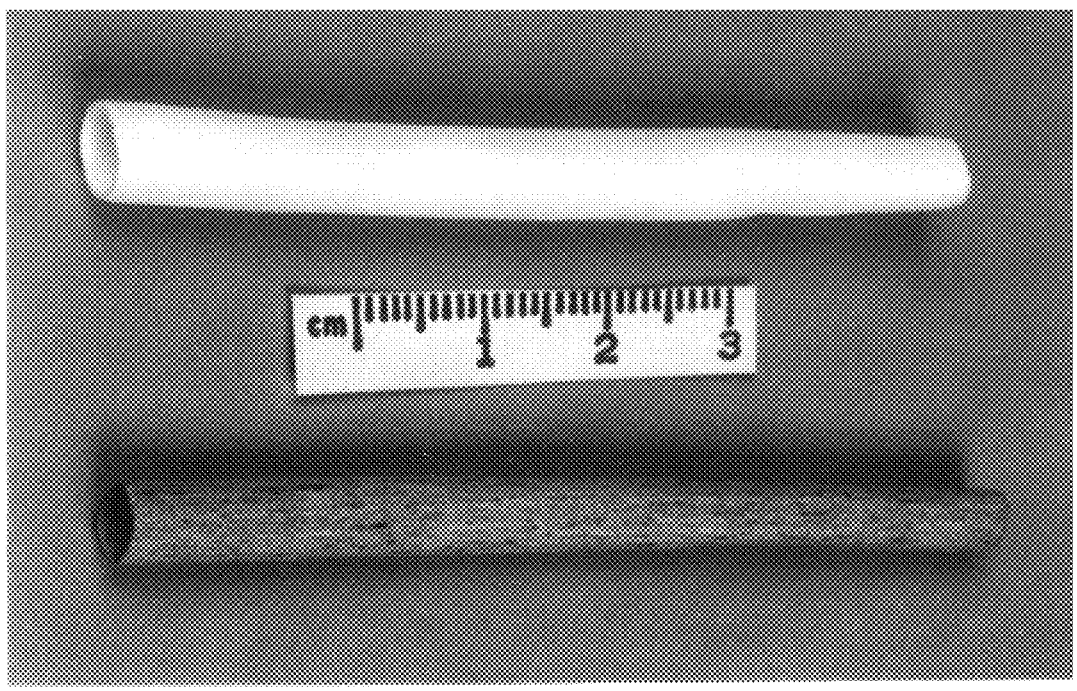
FIG. 1 illustrates grafts of PTFE and G-PTFE before implantation.

The presently preferred embodiment of the invention is a combination of expanded PTFE and graphite included in the framework of the PTFE lattice in a 9:1 ratio of PTFE powder and graphite.

Polytetrafluoroethylene in powder form may be obtained from E.I. DuPont de Nemours & Co., Inc., Wilmington, Del. Also further technical information on processing may be obtained from E.I. DuPont de Nemours & Co., Inc.

Graphite suitable for use in making the composition of this invention may be obtained from Acheson Colloids Company, Port Huron, Mich. under the tradename Dag-35 (0.8$\mu$) or Dag-154 (2.0$\mu$).

A particularly preferred prosthetic vascular device embodying the invention is formed from a tube of the composition of matter of this invention which is thereafter expanded according to the method of making a vascular device (without the incorporation of graphite) as described in detail in my co-pending U.S. application Ser. No. 517,415 filed Oct. 24, 1974.

Said application discloses methods and techniques for expanding PTFE. To review the disclosure adapted to this invention, the basic process for expanding graphite containing PTFE (G-PTFE) is as follows: The G-PTFE is first subjected to shear by, for example, extrusion into the desired geometrical configuration. The extrudate is then heated at a temperature below the sintering temperature at 327° C., and physically stretched or expanded along one axis. The expanded member is then physically restrained against contraction and is sintered by brief exposure to temperatures in excess of 327° C., thereby crystallizing the expanded structure and providing moderate tensile strength of up to approximately 6500 p.s.i. As the raw extrudate is stretched, the non-porous G-PTPE separates into solid nodes of G-PTFE which remains structurally interconnected by PTFE fibrils which are drawn from the nodes during expansion. Node size and distribution of final product are adversely affected by: very rapid expansion, uneven expansion, insufficient heating, non-uniform heating, and irregularly distribute expansion forces. The distance between nodes is directly proportional to the extent which the extrudate has been expanded. When PTFE is properly expanded along one axis, virtually no dimensional changes are observed in the orthogonal direction.

The manufacture of prosthetic vascular structures from the material of this invention is simple and can be performed with tore most rudimentary laboratory equipment, realizing, of course, that more sophisticated equipment is required for volume production and quality control. (The basic physical, chemical and procedural parameters for expanding PTFE without graphite are presented and discussed in Japanese Patent No. 13,560/67; however, an example will be given to illustrate the fundamental technique involved in making small bore PTFE grafts as an embodiment of this invention.)

A PTFE and graphite mixture as above described is extruded to form tubing having an average inside diameter of approximately 4 mm. and an average wall thickness of approximately 0.5 mm. The unsintered extrudate which is quite fragile is carefully cut with a razor blade in the lengths of, for example, 7.3 cm. Small aluminum plugs of virtually any configuration are inserted into the end of the tubing and secured thereto by tightly wrapped stainless steel wire. A relatively short end segment is thus confined between the inserted plug and the stainless steel wire. These plugs provide points for handling and attachment during the subsequent heating, elongation and sintering steps.

The tubing and plug assembly is placed into a uniformly heated oven for approximately one hour at 275° C. Thereafter, the assembly is removed from the oven, the plugs are grasped and stretched manually to obtain a tube length of 23 cm. The time required for removal and elongation should be made as short as possible to reduce the effects of cooling. Elongation should be carried out at a moderate, uniform rate and the plugs should be moved apart along a common axis of expansion to assure uniform force distribution. Typically, this manual operation has required less than ten seconds and has yielded good results.

The elongated assembly is then secured against contraction by restraining the plugs at the desired separation. This may be achieved in any number of ways, for example, by using plugs with enlarged ends which are placed in a fixture having U-shaped slots separated by the desired distance of 23 cm.

While still restrained, the elongated assembly is returned to the oven for approximately 45 seconds at 400° C., during which time the node/fibril superstructure is sintered and becomes fixed. The elongated grafts are then cut to the desired lengths and after sterilization and ready for implantation.

In large commercial applications, expansion is achieved mechanically in the oven itself at closely controlled rates and is immediately followed by sintering. However, excellent grafts are obtained by the simple laboratory techniques outlined above.

Fabrication of tapered grafts such as those used for peripheral artery replacement involves the additional step of reshaping a sintered tube of desired length and diameter over a tapered stainless steel mandrel which is then heated to approximately 300° C. After the entire assembly is allowed to cool, the slightly re-expanded graft retains the shape of the mandrel and may be removed for use without further heat treatment.

As an aid to a fuller understanding of the advantages of this invention, and disadvantages, examples are set out below:

EXAMPLE I

Nine parts by weight of dry powdered PTFE resin (Dupont extrusion grades, 200μ) is thoroughly mixed with one part by weight of 2 micron average diameter powdered graphite (Acheson Colloids Company, Port Huron, Mich., Dag 154). The ingredients are shaken together to obtain a homogeneous mixture. Thereafter, to the dry mixture is added 20% by weight (of the total mixture) VMP grade naptha. The wet mixture is compacted at 200 p.s.i/. to make a preform.

EXAMPLE II

Prosthetic vascular grafts made from the composition of this invention were tested according to the following protocol:

Large mongrel dogs were used as test subjects. An anaesthesia was used with intravenous thiamylal sodium and maintained with halothane. The common carotid and femoral arteries were used as test sites. Expanded PTFE grafts made according to the invention measuring 4 mm inside diameter and 4–5 cm in length, were interposed in each test site after excising a segment of artery. A graphite-PTFE (G-PTFE) graft was placed in one carotid and femoral artery position in each animal. A similar PTFE graft (without graphite) was placed in the alternate carotid and femoral artery. Whenever a G-PTFE was placed in a carotid position a G-PTFE graft was placed in a contralateral femoral position and a non-graphite PTFE "control" was provided for each G-PTFE implant site. In general the sites were reversed in each subsequent experiment in this manner, and an attempt was made to randomize positioning. Anastomoses were constructed in an end-to-end fashion using 6-0 monofilament polypropylene in a continuous whip stitch. Both anastomoses were completed prior to releasing the arterial occlusive clamps. No heparin was used throughout the experiment.

Graft harvest time distribution is listed in Table I. Grafts were harvested while the animal was under a general anaesthesia at between 11 and 390 days, with a mean harvest time of 136 days. A block of tissue containing the graft with a cuff of natural artery was dissected. Clamps were then rapidly applied to the artery and, without delay, a block was excised and submerged in ten percent formalin fixative solution. In a few instances this specimen was initially submerged in cold saline to permit taking gross specimen photographs. Immediately following this the specimen block was placed in the ten percent formalin fixative. Specimens were prepared by H&E staining for histological examination. In one instance, one-half of a G-PTFE graft and its control (390-days specimen) were fixed in glutaraldehyde and prepared for scanning electron photomicrographs.

TABLE I

Arterial Graft Harvest

| | | Months | | |
|---|---|---|---|---|
| <1 | 1–2 | 3–4 | 7–8 | 12–13 |

| DAYS | | | | |
|---|---|---|---|---|
| 11 | 48 | 94 | 217 | 378 |
| 22 | 52 | 122 | 228 | 390 |
| 27 | 57 | | | |

Range: 11 to 390 days
Mean: 136.3 days

The quantitative results are illustrated in Table II. A total of 54.2 percent (13/24) of the nongraphite PTFE grafts were patent and functioning at the time of harvest, whereas 79.2 percent (19/24) of the G-PTFE arterial substitutes were patent and functioning. There was only one instance when a G-PTPE arterial substitute had clotted in which the corresponding nongraphite PTFE control had not clotted. There were five instances when a nongraphite PTPE had clotted in which the corresponding graphite control remained patent.

TABLE II

GRAPHITE VS. NONGRAPHITE
EXPANDED PTFE ARTERIAL GRAFTS
(4 mm 1 D x 4–5 cm length)

| | Patency | | |
|---|---|---|---|
| | Carotid (%) | Femoral (%) | Total (%) |
| PTFE | 6/12 (50.0%) | 7/12 (58.3%) | 13/24 (54.2%) |
| Graphite PTFE | 8/12 (66.7%) | 11/12 (91.7%) | 19/24 (79.2%) |

Figure 4:
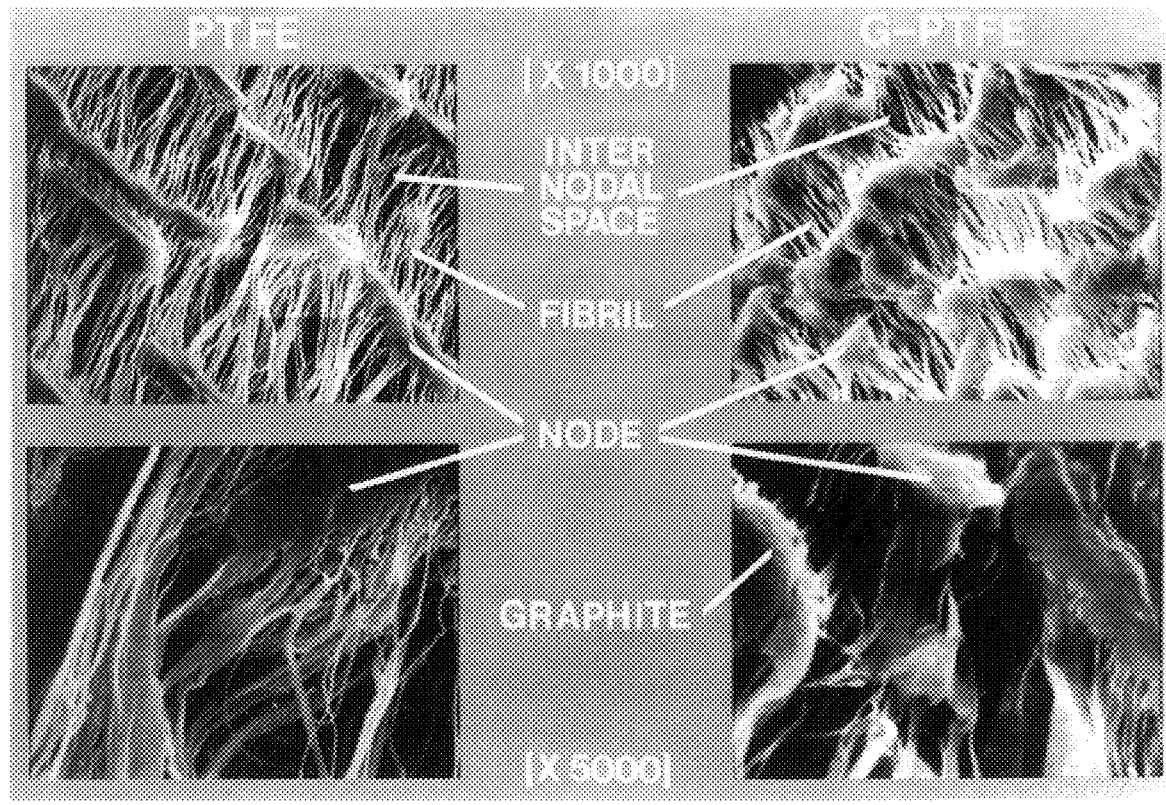
FIG. 4 illustrates the microscopic structure of a graphite PTFE arterial substitute and a non-graphite PTFE arterial substitute, compared side-by-side.

FIG. 4 illustrates the view of a higher powered scanning electron photomicrograph, wherein a qualitative difference appears in the PTFE nodes and fibrils. The G-PTFE nodes exhibit a fluffy appearance. The nodes edges appear somewhat less sharp and the fibrils slightly thicker when compared to the PTFE. Because the impression from this observation was that the graphite was actually incorporated in the PTFE, cross-sectional surface aspects of PTFE and G-PTFE grafts were viewed at 100-power. The G-PTFE nodes and fibrils were uniformly sparkling and gray in hue compared to the snow white appearance of the non-graphite PTFE (thereby confirming the conclusion that graphite is truly integrated in the PTFE).

Figure 2:
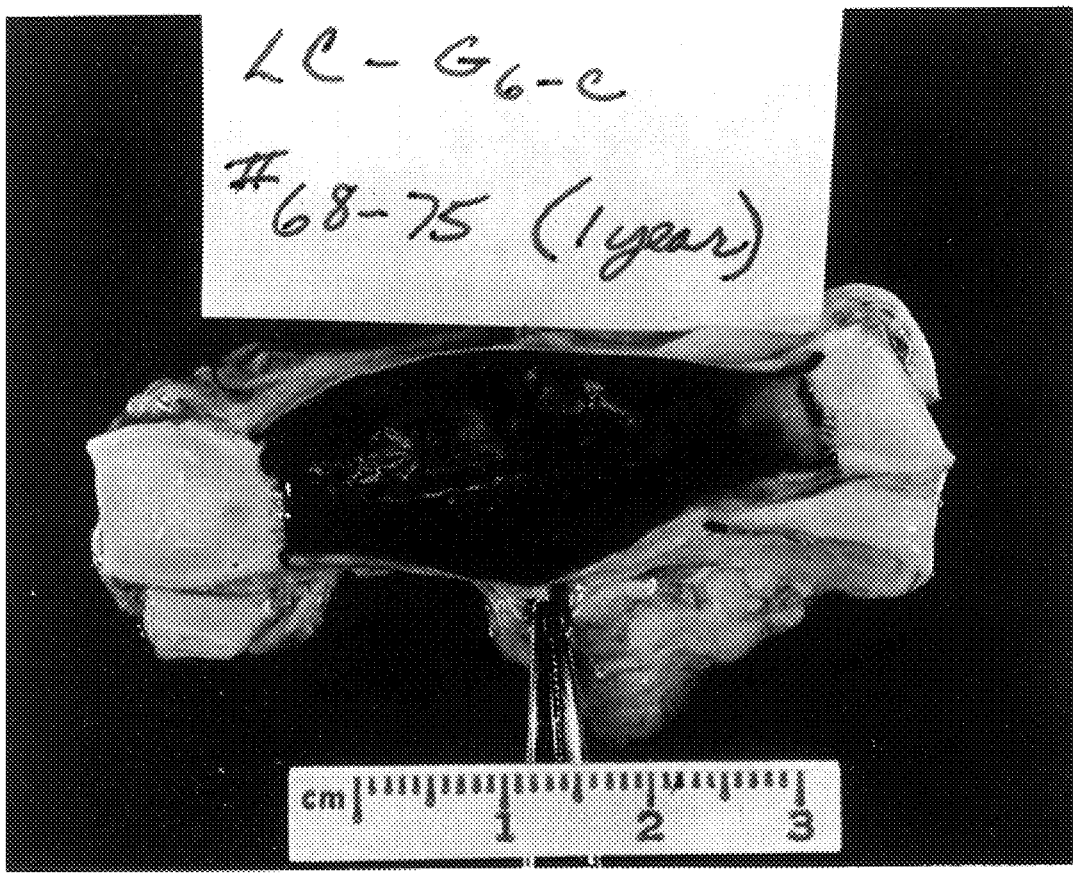
FIG. 2 illustrates a thoroughly healed specimen of G-PTFE graft harvested after more than twelve months.

FIG. 2 illustrates a healed specimen which was harvested after somewhat more than twelve months. A thin, uniform smooth intima spans the length of the graft and crosses both suture lines. The intima is thicker near the suture lines with the distinct margin extending from the edges of the suture inwardly towards mid-graph (approximately 4–6 mm) at which point the intima thins out considerably. This was a frequent finding.

Figure 3:
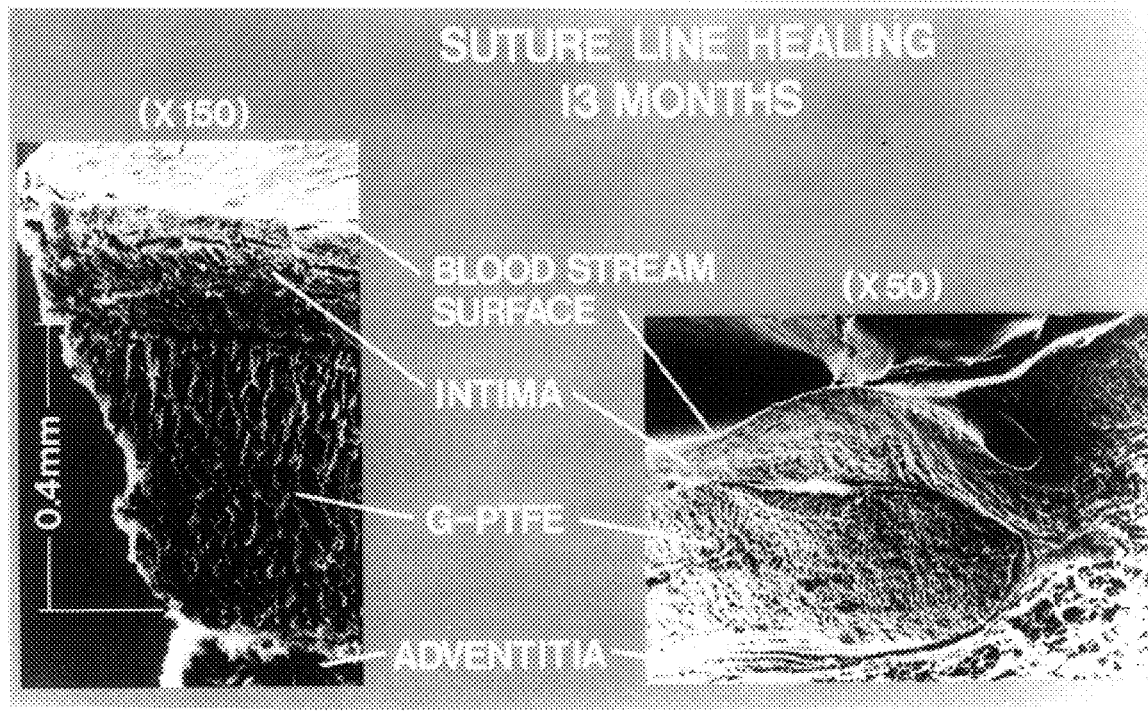
FIG. 3 illustrates a portion of FIG. 2 under a higher power scanning electron photomicrograph.

FIG. 3 demonstrates the incorporation of the graft at the suture line. Intima spans from the natural artery with a smooth transition across the suture line, and the ends of the graft are firmly in cased in fibrous tissue. The end-graft intima, although somewhat thicker than compared to the mid-graft intima, measures approximately 0.1–0.15 mm (100–150$\mu$). The suture line intima tapers gradually to a transition zone where there is rapid reduction in intima thickness over a short distance (approximately 1.0 mm) to the mid-graft intima thickness ranging from approximately 5–35 microns. The mid-graft intima contains elongated nucleated cells that resemble end-graft intima. In all areas the cells form an organized, stratified layer. The cells are more elongated and the flattened nuclei are oriented to the direction of the flow as they approach the bloodstream surface.

The mid-zone intima was often only one to two cells in thickness. In the earliest specimens amorphous debris and compacted fibrin bloodstream linings were noted. However, as the time period approached approximately sixty days, this layer became organized into a stratified cellular, structured intima as described above.

On the non-graphite PTFE were dense clumps containing red blood cells. However, on the G-PTFE intima red blood cells were sparsely distributed over the surface. The G-PTFE nodes were viewed through the intimal layer in the higher power. The nodes of the non-graphite PTFE ware not seen through the intima. In General, the mid-graph G-PTFE intima often consisted of only one to two cell thickness layer.

Non-graphite PTFE demonstrated firm collagenous adventitial attachment. This firm attachment developed rapidly to the non-graphite PTFE, usually within thirty days, whereas the G-PTFE adventitia demonstrated firm attachment at approximately sixty to ninety days. This attachment, however, was qualitatively comparable to the non-graphite PTFE. The adventitial attachment was composed of dense collagen which was observed to extend directly into the internodal spaces. Transmural cellular and fibrous replacement of the entire lattice structure occurred; and was observed equally throughout the G-PTFE and non-graphite PTFE, thereby demonstrating complete tissue incorporation of both types of grafts.

It was feared that graphite would leach out of the structure by continuous bloodstream washing, but graphite leaching did not occur: The growth and ultra structure appearance after thirteen months implantation was like that of the pre-implanted specimen. Compared to non-graphite PTFE there was a slight delay in the completed healing time for the G-PTFE (approximately sixty days after implantation). After this the graft demonstrated a smooth, stratified, cellular neointima which exposed the blood stream elements only to the organisms own tissues, thereby eliminating the potentially thrombogenic situation caused by inner action of blood and foreign material, However, it was noted that during harvest of the grafts only a brief period of blood stagnation (less than thirty seconds) permitted clumping of red blood cells and blood elements) on the intimal surface of the non-graphite PTFE. Surprisingly, this did not occur on the G-PTFE bloodstream surface. It is thought that the incorporated graphite continued to have an added effect of thromboresistance at the bloodstream-intima interface. The G-PTFE demonstrated qualitative healing comparable to that previously established for non-graphite PTFE grafts.

Overall, G-PTFE small artery substitutes demonstrated improved patency compared to the non-graphite PTFE. The evidence is that added thromboresistance imparted by the incorporation of negatively charged graphite into the expanded PTFE lattice produces the superior result. The PTFE lattice undergoes cellular fibrous ingrowth, and thus complete tissue incorporation of the graft occurred.

EXAMPLE III

Prosthetic venous grafts made of the material of this invention were made according to the teachings of the invention into tubes with an expansion ratio of 2:1 to 3:1. The wall thickness was approximately 1 mm. The lower expansion ratio plus increased wall thickness relative to the arterial substitute permitted somewhat less flexibility of the prosthesis, which in the venous position helps to avoid collapse of the substitute vessel. The prosthetic structure made according to this invention was tested according to the following protocol:

Graphite-PTFE prosthesis were placed in the superior vena cava position, i.e., from the junction of the right and left innominate vein to the right atrium. The substitutes were placed after this segment of vena cava had been removed. This position was chosen since the flow is extremely irregular and many characteristics of the flow pattern are factors which pre-disposed clotting. Consequently, the prosthetic vessel in this position was subjected to severe testing because (1) the fluctuating pressure phases of the cardiac cycle create irregularity of the flow in the superior vena cava including stasis, turbulence and blackflow; (2) there are no valves in this segment of the venous system which otherwise would insure forward flow only; (3) the fluctuating positive-negative pressure phases of the respiratory cycle also creates stasis-forward flow-backward flow and it is these pressure fluctuations that are transmitted through the superior vena cava; (4) the superimposition of the cardiac cycle pressure fluctuation with the respiratory cycle pressure fluctuation further predisposes to stagnation, turbulence and stasis; and (5) the net forward velocity of the flow in this venous segment is very low due to the very large cross-sectional area of the superior vena cava.

Nine superior vena cavae graphite-expanded PTFE grafts were implanted in dogs in the position previously described. Eight of the nine have remained patent for up to twenty months. In six additional dogs, superior vena cavae substitutes of non-graphite expanded PTFE were implanted and all six failed. Of the eight G-PTFE vena cavae, four currently exist in living animals and have remained patent from sixteen to twenty months after implantation. Four have been harvested and have been examined grossly and microscopically. As previously mentioned, all eight remained patent as evidenced by direct observation and angiography.

In relation venous applications the wall thickness is greater than arterial applications, as previously explained. The arterial thickness may range from 0.2 to 0.8 mm. whereas the venous should be 0.7 to 1.5 mm.

EXAMPLE IV

Material made according to the teachings of this invention was made into leaflet material for a prosthetic heart valve. The leaflet material was subjected to accelerate-testing under differential testing conditions which exceed the natural physiologic pressures for almost two years. Six leaflets (two assembled valves) have been tested to seventy-two million cycles without failure.

EXAMPLE V

Leaflets for prosthetic heart valves were constructed out of the material of this invention according to the teachings of this invention and were inserted in animal subjects for testing according to the following protocol:

Valves incorporating the leaflets were placed in the mitral and aortic valve positions in dogs and calves following removal of the animal's natural valves. Pressure measurements in the heart and circulation were recorded and determined to be within the normal physiological range of function.

Graphite PTFE was used as a sewing ring for the prosthetic valve. A tubular cuff was inverted on itself to provide a double thickness. This cuff forms a transition from the valve to the natural valve ring of the heart. The sewing ring can be fashioned to provide a transition from the prosthetic valve to the natural valve ring in various ways known to the art.

In Example I a ratio of 9:1 for PTFE:graphite was given. It should be understood that the ratios will vary according to the plastic and the negatively charged substances selected. The selections of materials and ratios will be governed by a consideration of the properties of the particular components selected, keeping in mind the teachings of this specification, with particular consideration given to three parameters concerning the negatively charged substances when the plastic is expanded, particularly PTFE, whether it be graphite or other, namely: (1) The geometric configuration of the lattice, e.g., PTFE, must not be altered outside of the specifications of the expanded PTFE as set out in my co-pending patent application above-identified; (2) the structural strength of the graft must not be compromised; and (3) the biological healing capacity must be preserved. In the case of PTFE:graphite ratios of about 5:1 to 15:1 should work.

Examples of preferred embodiments of the material, structures made from the material, and the method of making the material and the structures have been disclosed. From a consideration of the teachings of this disclosure persons ordinarily skilled in the art will perceive various and sundry modifications in addition to those specifically set forth above, all of which are embraced within the scope of this invention as pointed out by the appended claims.

What is claimed is:

1. A method of forming a vascular prosthetic structure having a bloodstream interface, the method comprising the steps of:

A. mixing polytetrafluoroethylene resin with a thromboresistance imparting amount of graphite powder to create a substantially homogeneous mixture;

B. compacting the mixture and forming a preform including the mixture;

C. extruding the preform to form an extrudate;

D. expanding the extrudate to form an expanded structure having a plurality of spaced nodes interconnected by fibrils;

E. sintering the expanded structure while restraining the expanded structure against contraction, to form the vascular prosthetic structure, whereby graphite is incorporated in the expanded structure in a thromboresisting amount at least at the bloodstream interfaces; and F. sterilizing the vascular prosthetic structure.

2. The method of forming a vascular prosthetic structure recited in claim 1, wherein step A includes mixing the resin and the powder so that a ratio of polytetrafluoroethylene to graphite is from about 5:1 to 15:1 by weight.

3. The method of forming a vascular prosthetic structure recited in claim 1, wherein step A includes mixing the resin and the powder so that a ratio of polytetrafluoroethylene to graphite is about 9:1 by weight.

4. The method of claim 1, wherein the vascular prosthetic structure is a tubular vascular graft, and wherein step C includes a step of extruding the preform to form a tubular extrudate.

5. The method of claim 2, wherein the vascular prosthetic structure is a tubular vascular graft, and wherein step C includes a step of extruding the preform to form a tubular extrudate.

6. The method of claim 3, wherein the vascular prosthetic structure is a tubular vascular graft, and wherein step C includes a step of extruding the preform to form a tubular extrudate.

7. The method recited in claim 1, further including a step of implanting the vascular prosthetic structure in a human body.

8. The method recited in claim 2, further including a step of implanting the vascular prosthetic structure in a human body.

9. The method recited in claim 3, further including a step of implanting the vascular prosthetic structure in a human body.

10. The method recited in claim 4, further including a step of implanting the vascular prosthetic structure in a human body.

* * * * *

Disclaimer 5,955,016 — David Goldfarb, Paradise Valley, AZ. METHOD OF FORMING A VASCULAR PROSTHETIC STRUCTURE INCLUDING EXPANDED PTFE AND GRAPHITE. Patent dated September 21, 1999. Disclaimer filed January 11, 2000, by the inventor.

The term of this patent shall not extend beyond the expiration date of Pat. No. 5,919,223.

*(Official Gazette, April 18, 2000)*